(12) United States Patent
Roberts et al.

(10) Patent No.: US 6,316,643 B1
(45) Date of Patent: Nov. 13, 2001

(54) PROCESS FOR THE PREPARATION OF DERIVATIVES OF FATTY ACIDS

(75) Inventors: Glyn Roberts, Wallasey; Cornelis Martinus Lok, Heswall; Christopher John Adams, Prenton; Kenneth Richard Seddon, Donaghadee; Martyn John Earle; Jennifer Therese Hamill, both of Belfast, all of (GB)

(73) Assignee: Unichema Chemie BV, Gouda (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,428

(22) PCT Filed: Jul. 7, 1997

(86) PCT No.: PCT/EP97/03641

§ 371 Date: Oct. 12, 1999

§ 102(e) Date: Oct. 12, 1999

(87) PCT Pub. No.: WO98/07679

PCT Pub. Date: Feb. 26, 1998

(30) Foreign Application Priority Data

Aug. 16, 1996 (EP) .................................................. 96305983

(51) Int. Cl.$^7$ ..................................................... C09F 7/00
(52) U.S. Cl. ........................................... 554/26; 554/156
(58) Field of Search ....................................... 554/156, 26

(56) References Cited

U.S. PATENT DOCUMENTS 3,090,807 * 5/1963 Illing et al. ........................... 554/156
4,371,469 * 2/1983 Foglia et al. ............................ 554/26

\* cited by examiner

*Primary Examiner*—Deborah D. Carr
(74) *Attorney, Agent, or Firm*—Pillsbury Winthrop LLP

(57) ABSTRACT

The preparation of a mixture comprising branched fatty acids and oligomerised fatty acids comprises contacting a source of unsaturated fatty acids or their derivatives with an ionic liquid.

22 Claims, No Drawings

PROCESS FOR THE PREPARATION OF DERIVATIVES OF FATTY ACIDS

The present invention relates to a process for the preparation of a mixture of branched and oligomeric fatty acids, by contacting a composition comprising unsaturated straight chain fatty acids with an ionic liquid. Fatty acids are versatile building blocks in various parts of the chemical industry, ranging from lubricants, polymers, solvents to cosmetics and much more. Fatty acids are generally obtained by hydrolysis of triglycerides of vegetable or animal origin. Naturally occurring triglycerides are esters of glycerol and generally straight chain, even numbered carboxylic acids, in size ranging from 10–24 carbon atoms. Most common are fatty acids having 12, 14, 16 or 18 carbon atoms. The fatty acids can either be saturated or contain one or more unsaturated bonds.

Long, straight chain saturated fatty acids (C10:0 and higher) are solid at room temperature, which makes them difficult to process in a number of applications. The unsaturated long chain fatty acids like e.g. oleic acid are liquid at room temperature, so easy to process, but are unstable because of the existence of a double bond. Derivatives of fatty acids that are branched (i.e. branched fatty acids) mimic the properties of the straight chain in many respects, however, they do not have the disadvantages associated with them. For example branched C18:0 (commercially known as isostearic acid) is liquid at room temperature, but is not as unstable as unsaturated C18:1, since the unsaturated bonds are prone to oxidation. Therefore, branched fatty acids are for many applications more desirable than straight chain fatty acids.

Apart from branched fatty acids other fatty acid derivatives, such as oligomerised fatty acids, find use in similar and other applications. Oligomeric fatty acids refer to materials prepared by coupling of the monomer units, of which typically dimeric and trimeric species are desired building blocks in plastics, the personal care industry, lubricants, etcetera.

Mixtures comprising oligomerised fatty acids and branched fatty acids can be likewise useful.

Currently, branched and oligomeric fatty acids are obtained by isomerisation/oligomerisation of the straight chain, unsaturated fatty acids. The reaction is conventionally carried out using a clay catalyst, and is generally performed at high temperature (e.g. 250° C.). A common process is the preparation of branched C18:0 and dimerised C18 (i.e. C36 dicarboxylic acids) from unsaturated straight chain C18:1 (or also C18:2). A disadvantage in this conventional process is that substantial amounts of aromatic dimers are formed. Such compounds are undesirable for a number of reasons, of which the most notable are: they do not contribute to the properties desired, and they can present a health hazard. The latter precludes the use of conventional dimer acids for certain highly desirable applications in the personal product and cosmetics industries.

In addition, the prior art processes suffer from the disadvantage that although a reasonable amount of polymerised product is obtained, the ratio of dimerised to trimerised and higher fatty acids is fixed and cannot easily be tuned to market demand.

Hence, there is a need for a process for the preparation of a mixture comprising branched and oligomeric fatty acids, in which mixture the concentration of aromatic dimers is low, or preferably substantially zero.

It has now been found that the above objectives can be met by a process for the preparation of a mixture comprising branched fatty acids and dimerised fatty acids, wherein a source comprising unsaturated fatty acids or derivatives thereof, is contacted with an ionic liquid.

An ionic liquid is herein to be understood as a salt (or a mixture of salts) in its liquid form (i.e. molten).

Preferably, to lead to the desired products, in the process according to the invention, the source comprises at least 50% by weight of fatty acids or derivatives thereof, having at least one unsaturated carbon-carbon bond in the fatty acid chain. It is also preferred that at least 50% by weight of said fatty acids or derivatives of fatty acids have a fatty acid chain length of between 8 and 24 carbon atoms. A preferred fatty acid in this respect is oleic acid or derivatives thereof.

Regarding the derivatives in the source as mentioned, esters are preferred, with alkylesters being the most preferred. Of these alkylesters, the most preferred ones are the fatty acid esters of alcohols having 1–4 carbon atoms, e.g. methanol, ethanol, propanol. Hence, a preferred source for performing the reaction according to the invention comprises oleic acid, methyl oleate, and/or ethyl oleate.

With respect to the type of ionic liquid, a wide variety of possibilities exists. However, it will be clear that the preferred ionic liquids are the ones that are liquid at relatively low temperatures. Although some salts have very high melting points (i.e. common NaCl has a melting point of approx. 850° C.), there are salts known which melt under less severe conditions. An example of such salts are mixtures of two or more salts. In the case in which a mixture of two salts is used, the resulting ionic liquid is called a binary ionic liquid. Hence, it is preferred that in the process as set out above the ionic liquid comprises a binary ionic liquid.

Preferred binary ionic liquids comprise a metal(III) chloride and/or an organic halide salt, e.g. $[A]^+X^-$. Also, inorganic halide salts can be used. Suitable metal (III) chlorides include aluminium (III) chloride and iron (III) chloride. Regarding the organic halide, an unsymmetrical imidazolium or pyridinium halide has the advantage that isomerisation/oligomerisation may now occur under mild conditions, contrary to conventional processes. A preferred unsymmetrical imidazolium halide is 1-methyl-3-ethyl imidazolium chloride.

A distinct advantage of the presently invented process over the known processes is that there is no need to carry out a reaction for branching and/or oligomerisation of fatty acids at elevated temperatures: as long as the temperature is high enough for the salt which is used as the reaction "solvent" (or medium) to be in its liquid form (i.e. molten). An additional advantage is that substantially no aromatic and/or cyclic dimers are formed in the process according to the invention.

Therefore, it is preferred that the process according to the invention is carried out at temperatures below 250° C. More preferred are operating temperatures of below 150° C., or even below 50° C., as long as the ionic liquid is chosen such that the mixture of ionic liquid and reactants is a liquid. Some reaction systems are even active at temperatures below 0° C. At such temperatures, the amount at cracked products obtained can be low, and following this, such a temperature can be preferred for some cases.

As an additional advantage, there is no need for performing the reaction under increased pressure, and therefore, it is preferred for the reaction according to the invention to be carried out at atmospheric pressure.

Yet a further advantage of the present process is that long reaction times are not needed. Generally, the reaction can be shorter than 60 minutes, in many cases even shorter than 15 minutes.

In the process according to the invention, the ratio of ionic liquid: fatty acid reactant is preferably larger than 1:1, preferably at least 3:1, and most preferably at least 6:1.

In a practical set up, the process will be preferably be operated in a (semi-) continuous way, and the products are separated from the reactants and ionic liquid. The expensive unsymmetrical imadazolium or pyridinium halide can be easily separated from the product by extraction with solvents such as dichloromethane and hexane etc, together with mixtures thereof. The imidazolium or pyridinium species can then be recycled following evaporation or distillation of the solvent.

The invention is further illustrated by the following examples, which are not to be interpreted as limiting the invention thereto.

EXAMPLE 1

Branching/oligomerisation of methyl oleate.

In a dry box, 1-methyl-3-ethylimidazolium chloride (3.55 g, 24.20 mmol) was added to triply sublimed aluminium (III) chloride (6.45 g, 48.40 mmol), in a 100 $cm^3$ round bottomed flask, equipped with a dinitrogen inlet, Teflon stirrer bar and a stopper. The two solids were left to stand for 1 h without stirring, at which point the melt had partially formed. The melt was transferred to a fume cupboard and connected to a supply of dinitrogen, and cooled to a reaction temperature of 0° C. Methyl oleate (3.56 g, 12.10 mmol, molar ratio of ionic liquid to methyl oleate 6:1) was added dropwise by pipette over a 10 minute period, and the whole system kept under a constant stream of dinitrogen to prevent air/moisture entering the reaction. The reaction was allowed to proceed for 1hr, at which point the reaction mixture was quenched by the addition of water and crushed ice (50 $cm^3$). The resultant organic phase was then extracted with 3×30 $cm^3$ aliquots of dichloromethane. The combined organic extracts were dried using $MgSO_4$, filtered, and the solvent evaporated using a rotary evaporator.

The various products were separated by flash chromatography on 100 g of silica, using a gradient elution (500 ml of 2%, followed by 5%, followed by 10% ethyl ethanoate in 40–60° petroleum ether.) Following separation the products were identified by a combination of $^1H$ & $^{13}C$ NMR, GCMS and infra-red.

Selectivities for the various products obtained under these conditions are presented in Table 1. This table also outlines the results of other experiments performed in the same manner as outlined in this example but using various ionic liquid: methyl oleate ratios, reaction times and reaction temperatures.

Selectivity to branched/oligomeric fatty esters can be tailored to demand by controlling either the reaction rate or the ratio of ionic liquid: fatty acid reactant. Short reaction times and low temperatures favouring the production of branched monomer and dimer moieties, long reaction times/high temperatures favouring the production of trimer and higher polymeric species. Similarly high dilution of the unsaturated fatty ester feedstocks in the ionic liquid catalyst/solvent system favour the production of branched and dimer moieties.

Analysis of the dimer fractions obtained from all these experiments, by NMR, revealed the complete absence of cyclic or aromatic structures.

TABLE 1

Effective of ionic liquid:reactant mole ratio, reaction temperature and reaction on time on product selectivity

| Mol rat. | Temp/ ° C. | Reac. time mins | % BM | % LM | % DIM | % TRIM | % Poly | % Crac |
|---|---|---|---|---|---|---|---|---|
| 3:1 | −40 | 10 | 26 | 1 | 38 | 19 | <10 | 0 |
| 3:1 | 0 | 10 | 20 | 1 | 19 | 30 | <20 | 5 |
| 1.1:1 | −40 | 10 | 17 | 1 | 18 | 43 | 20 | 0 |
| 1.1:1 | 25 | 10 | 25 | 2 | 14 | 32 | 20 | 0 |

(BM = Branched monomer, LM = Linear monomer, DIM = Dimer, TRIM = trimer, Poly = Polymer, Crac = Cracked products)
*Note the oligomeric fractions in this experiment were not separated.

The cracked products observed are sweet smelling volatile low molecular fatty acid esters.

EXAMPLE 2

Effect of reaction temperature

Example 1 has been repeated using the same conditions, except that the ionic liquid: fatty acid reactant ratio is now 6:1, and the reaction has been performed at various temperatures (see table 2). All other conditions remained the same.

TABLE 2

Effect of temperature at a ionic liquid: fatty acid reactant ratio = 6:1

| Temperature/° C. | % Monomer | % Dimer | % Trimer & higher polymers | % Cracked products |
|---|---|---|---|---|
| −40 | 13.5 | .5 | 80.9 | 1.1 |
| −10 | 17.4 | 3.2 | 54.6 | 24.7 |
| 0 | 18.3 | 6 | 49.3 | 26.4 |
| 8 | 21.1 | 5.3 | 50.3 | 23.3 |
| 25 | 20.5 | 15.7 | 43.8 | 19.9 |
| 50 | 16.1 | 9.6 | 34.6 | 39.7 |
| 60 | 14 | 11.4 | 33.5 | 41.1 |
| 120 | 11.9 | 5.8 | 32.3 | 50.0 |

EXAMPLE 3

Effect of water addition

In a dry box, 1-methyl-3-ethylimidazolium chloride (3.55 g, 24.20 mmol) was added to a triply sublimed aluminium (III) chloride (6.45 g, 48.40 mmol) in a 100 $cm^3$ round bottomed flask, equipped with a dinitrogen inlet, Teflon stirrer bar and a stopper. The two solids were left to stand for 1 h without stirring (to avoid excessive reaction rate and heat build up) until the melt had partially formed. The melt was then stirred for 4 h at which point the aluminium (III) chloride had reacted. The melt was then transferred to a fume cupboard to and connected to a supply of dinitrogen. A mixture of methyl oleate (3,50 g, 12.0 mmol, 50 mmol %) and water (0.10 g, 0.1 ml) was added dropwise and stirred at room temperature for 1.5 h. Water and crushed ice (50 $cm^3$) was added and the product was extracted with dichloromethane (3×30 $cm^3$). The combined organic extracts were dried ($MgSO_4$), filtered and the solvent evaporated on a rotary evaporator. This gave 3.10 g of a straw coloured oil.

The various products were separated by flash chromatography on 100 g of silica, using a gradient elution (500 ml of 2%, followed by 5%, followed by 10% ethyl ethanoate in 40–60° petroleum ether.) Following separation the products were identified by a combination of $^1$H & $^{13}$C NMR, GCMS and infra-red.

Selectivities for the various products obtained under these conditions are listed below:

| | |
|---|---|
| Cracked products*: | 21% |
| Monomer + dimer: | 38% |
| Trimer + polymer: | 42% |

*the cracked products comprise mainly branched fatty acids having between 7 and 18 carbon atoms. NMR analysis of the dimer fractions reveals the absence of cyclic or aromatic structures.

EXAMPLE 4

Alternative extraction to preserve 1-methyl-3-ethylimadazolium chloride

In a dry box, 1-methyl-3-ethylimadazolium chloride (3.55 g, 24.20 mmol) was added to doubly sublimed aluminium (III) chloride (6.45 g, 48.40 mmol) in a 100 cm$^3$ round bottomed flask, equipped with a dinitrogen inlet, Teflon stirrer bar and a stopper. The two solids were left to stand for 0.5 hour without stirring (to avoid excessive reaction rate and heat build up) until the melt had partially formed. The melt was then stirred for 3 hours until all the aluminium (III) chloride had reacted. The melt was transferred to a fume cupboard and connected to a supply of dinitrogen. The reaction vessel was cooled to 0° C. with an ice bath and methyl oleate (3.0 g, 10.0 mmol, 30w/w %) was added dropwise over a fifteen minute period. After a further 5 mins, dichloromethane (25 cm$^3$) was added and the product extracted with hexane (3×33 cm$^3$ aliquots). The solvent was evaporated from the combined organic extracts to give 3.31 g of the aluminium adduct of the products. A further 0.84 g of adduct was obtained by washing the melt with 3×33 cm$^3$ aliquots of 50:50 dichloromethane/hexane, followed by evaporation of the solvent. The adducts were destroyed by addition of water (50 ml), extracted with dichloromethane (2×20 ml), dried (MgSO$_4$), filtered and the solvent evaporated on a rotary evaporator. This gave a total of 2.37 g of colourless oil (79% of starting product-Remainder is accounted for by volatile products produced as a consequence of cracking reactions). The extracts were separated by Kugelrohr distillation at 2 mmHg pressure.

| | |
|---|---|
| Cracked products*: | 21% |
| Monomer: | 14% |
| Dimer: | 8% |
| Trimer + Polymer: | 57% |

*the cracked products comprise mainly branched fatty acids having between 7 and 18 carbon atoms. Analysis of the dimer fraction by NMR indicates the absence of cyclic or aromatic dimer structures.

EXAMPLE 5

Effect of iron based ionic liquid on fatty acid oligomerisation

Preparation of 58% Iron (III) Chloride

In a dry-box, triply sublimed FeCl$_3$ (8.96 g, 55.2×10$^{-3}$ mol) was added to 1-ethyl-3-methyl imidazolium chloride (5.86 g, 40×10$^{-3}$ mol). The two solids were left stirring overnight.

Oligomerisation of methyl oleate in 58% FeCl$_3$-[emim] Cl

In a dry box, 58% FeCl$_3$-[emim] Cl (14.82, 40×10$^{-3}$ mol) was transferred to a 3-necked 200 ml round-bottomed flask equipped with a dinitrogen inlet, Teflon stirrer bar and stoppers. The melt was transferred to a fume cupboard and connected to a supply of dinitrogen. Methyl oleate (3.0 g, 3.4 cm$^3$, 10×10$^{-3}$ mol) was added dropwise over a 10 minute period. The reaction mixture was left stirring overnight. A sample was then removed from the reaction mixture and quenched with distilled water. The product was extracted with dichloromethane, dried (MgSO$_4$) and the solvent removed on a rotary evaporator. The sample was analysed by proton NMR which indicated that the reaction was complete. The NMR also showed that some chlorination had occurred. Distilled water was added to the bulk mixture to quench the combined organic extracts were dried (MgSO$_4$), filtered and the solvent removed on a rotary evaporator.

A sample of the crude product (0.71 g) was separated by fractional distillation under vacuum (2.0 mmHg) on a Kugelrohr apparatus. This produced the following yields:

| | |
|---|---|
| Monomer | 0.23 g (32.4%) |
| Dimer | 0.06 g (8.5%) |
| Trimer + polymer | 0.28 g (39.4%) |
| Cracked products | 0.14 g (19.7%) |

Crude Product $^1$H NMR (500 MHz/CDCl$_3$/TMS) (δ/ppm) 0.85–0.89 (d+t, 4H), 1.28–1.29 (m, 28H), 1.61 (m, 2H), 2.28–2.33 (t, 2H), 3.66–3.67 (s, 3H), 3.87–3.89 (m, 0.3H).

$^{13}$C NMR (75 MHz/CDCl$_3$/TMS) (δ/ppm) 14.548, 23.103, 25.397, 25.580, 26.920, 29.584, 29.674, 29.736, 30.057, 32.002, 32.334, 34.582, 38.959, 52.064, 64.787, 174.763

Note that GCMS showed that there was a high proportion (estimated to be 50%) of the monomer which had been chlorinated. A breakdown of the products detected by GCMS results is given below:

| Retention time/s | M$^+$ | Product |
|---|---|---|
| 544–552 | 242 | C$_{14}$ Methyl ester |
| 580–591 | 256 | C$_{15}$ Methyl ester |
| 612–631 | 270 | C$_{16}$ Methyl ester |
| 654–657 | 284 | C$_{17}$ Methyl ester |
| 688–734 | 298 | C$_{18}$ Methyl ester |
| 766–881 | 332 | Chlorinated C$_{18}$ Methyl ester |

What is claimed is:

1. Process for the preparation of a mixture comprising branched fatty acids and oligomerised fatty acids, wherein a source comprising unsaturated fatty acids or derivatives thereof, is contacted with a salt or mixture of salts in liquid form.

2. Process according to claim 1, characterized in that the source comprises at least 50% by weight of fatty acids or derivatives thereof, having at least one unsaturated carbon-carbon bond in the fatty acid chain.

3. Process according to claim 2, characterized in that the fatty acid feedstock or derivative thereof, comprises of at least 80% by weight of unsaturated fatty acid or derivatives thereof.

4. Process according to claim 1, characterized in that at least 50% by weight of fatty acids or derivatives thereof have a fatty acid chain length of between 10 and 24 carbon atoms.

5. Process according to claim 4, characterized in that the fatty acid feedstock or derivative thereof comprises at least 40% by weight of oleic acid or derivative thereof.

6. Process according to claim 5, characterized in that the fatty acid feedstock or derivative thereof comprises of at least 70% by weight of oleic acid.

7. Process according to claim 1, characterized in that the fatty acid derivative is an alkyl ester of a fatty acid.

8. Process according to claim 7, characterized in that the fatty acid derivative is an ester of fatty acid and an alcohol having 1–4 carbon atoms.

9. Process according to claim 1, characterized in that the salt or mixture of salts in liquid form comprises a binary salt.

10. Process according to claim 1, characterized in that the salt or mixture of salts in liquid form comprises a metal (III) chloride and/or an organic halide.

11. Process according to claim 10, characterized in that the metal (III) chloride is aluminium (III) or iron (III) chloride.

12. Process according to claim 10, characterised in that the organic halide is an unsymmetrical imidazolium halide or a pyridinium halide.

13. Process according to claim 12, characterized in that the unsymmetrical imidazolium halide is 1-methyl-3-ethylimidazolium chloride.

14. Process according to claim 1, characterized in that it is carried out at temperatures below 150° C.

15. Process according to any of claim 1, characterized in that the reaction is performed under atmospheric pressure.

16. Process according to claim 1, characterized in that the salt or mixture of salts in liquid form: fatty acid reactant ratio is larger than 1:1.

17. Process according to any of claim 1, characterized in that substantially no aromatic dimers are produced during the reaction.

18. Process according to claim 1 in which the products are separated from the reactants and salt or mixture of salts in liquid form.

19. Process according to claim 18 in which the imadazolium or pyridinium halide is separated from the product/$AlCl_3$ adduct by extraction with a polar solvent.

20. Process according to claim 18 in which the product is liberated from the product/$AlCl_3$ adduct by hydrolysis in water.

21. Process according to claim 1, characterized in that it is carried out at temperatures below 50° C.

22. Process according to claim 1, characterized in that the salt or mixture of salts in liquid form: fatty acid reactant ratio is at least 3:1.

* * * * *